United States Patent
Falster et al.

(10) Patent No.: US 6,689,209 B2
(45) Date of Patent: Feb. 10, 2004

(54) PROCESS FOR PREPARING LOW DEFECT DENSITY SILICON USING HIGH GROWTH RATES

(75) Inventors: Robert J. Falster, London (GB); Vladimir Voronkov, Merano (IT)

(73) Assignee: MEMC Electronic Materials, Inc., St. Peters, MO (US)

(*) Notice: Subject to any disclaimer, the term of this patent is extended or adjusted under 35 U.S.C. 154(b) by 90 days.

(21) Appl. No.: 09/871,255

(22) Filed: May 31, 2001

(65) Prior Publication Data

US 2002/0053315 A1 May 9, 2002

Related U.S. Application Data

(60) Provisional application No. 60/245,610, filed on Nov. 3, 2000.

(51) Int. Cl.[7] .............................. C30B 33/02
(52) U.S. Cl. .............................. 117/2; 117/3
(58) Field of Search ................... 117/2, 3, 13

(56) References Cited

U.S. PATENT DOCUMENTS

| 5,935,320 A | * | 8/1999 | Graef et al. ................. 117/2 |
| 6,045,610 A | * | 4/2000 | Park et al. ................... 117/3 |
| 6,129,787 A | * | 10/2000 | Adachi et al. ............... 117/89 |

FOREIGN PATENT DOCUMENTS

| EP | 0 990 718 A1 | 4/2000 | |
| GB | 2137524 A | * 10/1984 | .......... C30B/33/00 |
| WO | WO 00/00675 A1 | 1/2000 | |

OTHER PUBLICATIONS

Wolf et al., Silicon for the VLSI Era vol. 1: Process Technology, Chapter 2, Lattice Press, Sunset Beach, CA, USA, 1986.*

PCT/US01/43044 PCT International Search Report completed Nov. 27, 2002.

* cited by examiner

Primary Examiner—Robert Kunemund
Assistant Examiner—Matthew Anderson
(74) Attorney, Agent, or Firm—Senniger, Powers, Leavitt & Roedel

(57) ABSTRACT

The present invention relates to a process for growing a single crystal silicon ingot which contains an axially symmetric region which is substantially free of agglomerated intrinsic point defects. The process comprises (i) forming a region within the constant diameter portion in which vacancies are the predominant intrinsic point defect; (ii) heating the lateral surface of the ingot to cause a thermally induced inward flux of silicon self interstitial atoms into the region from the heated surface which reduces the concentration of vacancies in the region; and (iii) maintaining the temperature of the region in excess of the temperature, $T_A$, at which agglomeration of vacancy point defects into agglomerated defects occurs during the period of time between the formation of the region and the reduction of the concentration of vacancies in the region.

47 Claims, 3 Drawing Sheets

COMPARISON BETWEEN B-DEFECTS IN A WAFER SUBJECTED TO THE TREATMENT OF THE PRESENT INVENTION WITH THE B-DEFECTS IN A WAFER NOT SUBJECTED TO A HEAT TREATMENT

PROCESS FOR PREPARING LOW DEFECT DENSITY SILICON USING HIGH GROWTH RATES

CROSS-REFERENCE TO RELATED APPLICATION

This application claims priority from U.S. provisional application, Ser. No. 60/245,610, filed Nov. 3, 2000.

BACKGROUND OF THE INVENTION

The present invention generally relates to the preparation of semiconductor grade single crystal silicon which is used in the manufacture of electronic components. More particularly, the present invention relates to a process for preparing single crystal silicon ingots which are substantially free of vacancy-type agglomerated intrinsic point defects, as well as wafers obtained therefrom, wherein said ingots are grown at rates which would otherwise result in the formation of agglomerated vacancy-type intrinsic point defects within the ingots.

Single crystal silicon, which is the starting material for most processes for the fabrication of semiconductor electronic components, is commonly prepared by the so-called Czochralski ("Cz") method. In this method, polycrystalline silicon ("polysilicon") is charged to a crucible and melted, a seed crystal is brought into contact with the molten silicon and a single crystal is grown by slow extraction. After formation of a neck is complete, the diameter of the crystal is enlarged by decreasing the pulling rate and/or the melt temperature until the desired or target diameter is reached, thus forming a seed cone. The cylindrical main body of the crystal, which has an approximately constant diameter, is then grown by controlling the pull rate and the melt temperature while compensating for the decreasing melt level. Near the end of the growth process but before the crucible is emptied of molten silicon, the crystal diameter must be reduced gradually to form an end-cone. Typically, the end-cone is formed by increasing the crystal pull rate and heat supplied to the crucible. When the diameter becomes small enough, the crystal is then separated from the melt.

In recent years, it has been recognized that a number of defects in single crystal silicon form in the crystal growth chamber as the crystal cools after solidification. Such defects arise, in part, due to the presence of an excess (i.e. a concentration above the solubility limit) of intrinsic point defects, which are known as vacancies and self-interstitials. Silicon crystals grown from a melt are typically grown with an excess of one or the other type of intrinsic point defect, either crystal lattice vacancies ("V") or silicon self-interstitials ("I"). It has been suggested that the type and initial concentration of these point defects in the silicon are determined at the time of solidification and, if these concentrations reach a level of critical supersaturation in the system and the mobility of the point defects is sufficiently high, a reaction, or an agglomeration event, will likely occur. Agglomerated intrinsic point defects in silicon can severely impact the yield potential of the material in the production of complex and highly integrated circuits.

Vacancy-type defects are recognized to be the origin of such observable crystal defects as D-defects, Flow Pattern Defects (FPDs), Gate Oxide Integrity (GOI) Defects, Crystal Originated Particle (COP) Defects, crystal originated Light Point Defects (LPDs), as well as certain classes of bulk defects observed by infrared light scattering techniques such as Scanning Infrared Microscopy and Laser Scanning Tomography. Also present in regions of excess vacancies are defects which act as the nuclei for ring oxidation induced stacking faults (OISF). It is speculated that this particular defect is a high temperature nucleated oxygen agglomerate catalyzed by the presence of excess vacancies.

Defects relating to self-interstitials are less well studied. They are generally regarded as being low densities of interstitial-type dislocation loops or networks. Such defects are not responsible for gate oxide integrity failures, an important wafer performance criterion, but they are widely recognized to be the cause of other types of device failures usually associated with current leakage problems.

The density of such vacancy and self-interstitial agglomerated defects in Czochralski silicon historically has been within the range of about $1*10^3/cm^3$ to about $1*10^7/cm^3$. While these values are relatively low, agglomerated intrinsic point defects are of rapidly increasing importance to device manufacturers and, in fact, are now seen as yield-limiting factors in device fabrication processes.

One approach which has been suggested to control the formation of agglomerated defects is to control the initial concentration of the point defects when the single crystal silicon is formed upon solidification from a molten silicon mass by controlling the pull rate (v) of the single crystal silicon ingot from the molten silicon mass, wherein higher pull rates tend to produce vacancy rich material and lower pull rates tend to produce interstitial rich material, and controlling the axial temperature gradient, G, in the vicinity of the solid-liquid interface of the growing crystal for a given temperature gradient. In particular, it has been suggested that the radial variation of the axial temperature gradient be no greater than 5° C./cm or less. (See, e.g., Iida et al., EP0890662) This approach, however, requires rigorous design and control of the hot zone of a crystal puller.

Another approach which has been suggested to control the formation of agglomerated defects is to control the initial concentration of vacancy or interstitial point defects when the single crystal silicon is formed upon solidification from a molten silicon mass, and then controlling the cooling rate of the crystal from the temperature of solidification to a temperature of about 1,050° C. to permit the diffusion of silicon self-interstial atoms or vacancies and thereby maintain the supersaturation of the vacancy system or the interstitial system at values which are less than those at which agglomeration reactions occur (See, e.g., Falster et al., U.S. Pat. No. 5,919,302 and Falster et al., WO 98/45509). It is generally accepted however that vacancies diffuse as a much slower rate than silicon self-interstitials. Thus, while this approach may be successfully used to prepare single crystal silicon which is substantially free of agglomerated vacancy or interstitial defects, the time required to allow for adequate diffusion of vacancies reduces the benefit of the increased growth velocity, while the decreased growth velocity required to produce interstitial dominated ingots reduces the benefit of the decreased cool down time required to allow diffusion of interstitials. This may have the effect of reducing the throughput for the crystal puller.

SUMMARY OF THE INVENTION

Among the several objects and features of the present invention may be noted the provision of a process for preparing a single crystal silicon ingot, as well as wafers obtained therefrom, having a region which is substantially free of agglomerated defects; the provision of such a process wherein vacancies are initially the predominant intrinsic point defect within the region; the provision of such a process wherein the vacancy concentration in the region is reduced after solidification through recombination with silicon self-interstitials injected from a lateral surface on the constant diameter portion of the ingot; the provision of such a process wherein the injection of interstitials is achieved by thermally inducing a flux of interstitials during ingot growth; the provision of such a process wherein the thermally induced flux of interstitials is achieved after the ingot is separated from the melt; the provision of such a process wherein the vacancy dominated region is converted to a region wherein interstitials predominate; the provision of such a process which does not substantially diminish the throughput of the crystal puller; the provision of such a process which substantially reduces pull rate limitations of the crystal puller in the production of the defect-free silicon ingots; and, the provision of such a process which substantially reduces the average axial temperature gradient $G_o$ limitations of the crystal puller.

Briefly, therefore, the present invention is directed to a process for growing a single crystal silicon ingot having a central axis, a seed-cone, an end-cone, a constant diameter portion between the seed-cone and the end-cone, and a region which comprises a fraction of the constant diameter portion of the ingot and which is substantially free of agglomerated intrinsic point defects. The ingot is grown from a silicon melt in accordance with the Czochralski method, the process comprising (i) forming a region within the constant diameter portion in which vacancies are the predominant intrinsic point defect, (ii) heating the lateral surface of the ingot to a temperature in excess of the temperature of the region to cause an inward flux of silicon self interstitial atoms into the region from the heated surface which reduces the concentration of vacancies in the region, and (iii) maintaining the temperature of the region in excess of the temperature, $T_A$, at which agglomeration of vacancy point defects into agglomerated defects occurs during the period of time between the formation of the region and the reduction of the concentration of vacancies in the region.

The present invention is further directed to a process for growing a single crystal silicon ingot having a central axis, a seed-cone, an end-cone, a constant diameter portion between the seed-cone and the end-cone, and a region which comprises a fraction of the constant diameter portion of the ingot and which is substantially free of agglomerated intrinsic point defects. The ingot is grown from a silicon melt in accordance with the Czochralski method, the process comprising (i) forming a region within the constant diameter portion in which vacancies are the predominant intrinsic point defect, (ii) heating the lateral surface of the ingot to a temperature in excess of the temperature of the region to cause an inward flux of silicon self interstitial atoms into the region from the heated surface which transforms the region from a vacancy dominated region to an interstitial dominated region, and (iii) maintaining the temperature of the region in excess of the temperature, $T_A$, at which agglomeration of vacancy point defects into agglomerated defects occurs during the period of time between the formation of the region and the reduction of the concentration of vacancies in the region.

The present invention is still further directed to a process for growing a single crystal silicon ingot having a central axis, a seed-cone, an end-cone, a constant diameter portion between the seed-cone and the end-cone, and a region which comprises a fraction of the constant diameter portion of the ingot and which is substantially free of agglomerated intrinsic point defects. The ingot is grown from a silicon melt in accordance with the Czochralski method, the process comprising (i) forming a region within the constant diameter portion in which vacancies are the predominant intrinsic point defect, (ii) heating the lateral surface of the ingot to a temperature in excess of the temperature of the region to cause an inward flux of silicon self interstitial atoms into the region from the heated surface which transforms the region from a vacancy dominated region to a interstitial dominated region wherein the concentration of interstitials is at least about the saturation concentration required to cause agglomeration of interstitials upon conventional cooling of the ingot (iii) maintaining the temperature of the region in excess of the temperature, $T_A$, at which agglomeration of vacancy point defects into agglomerated defects occurs during the period of time between the formation of the region and the reduction of the concentration of vacancies in the region, and (iv) controlling the cooling of the region through the temperature range at which agglomerated interstitials may nucleate to suppress the concentration of the interstitials therein such that agglomerated interstitials do not form upon cooling the ingot.

The present invention is still further directed to a process for growing a single crystal silicon ingot having a central axis, a seed-cone, an end-cone, a constant diameter portion between the seed-cone and the end-cone, and a region which comprises a fraction of the constant diameter portion of the ingot and which is substantially free of agglomerated intrinsic point defects. The ingot is grown from a silicon melt in accordance with the Czochralski method, the process comprising (i) forming a region within the constant diameter portion in which vacancies are the predominant intrinsic point defect, (ii) heating the lateral surface of the ingot to a temperature in excess of the temperature of the region to cause an inward flux of silicon self interstitial atoms into the region from the heated surface which transforms the region from a vacancy dominated region to a interstitial dominated region wherein the concentration of interstitials is at least about the saturation concentration required to cause agglomeration of interstitials upon conventional cooling of the ingot (iii) maintaining the temperature of the region in excess of the temperature, $T_A$, at which agglomeration of vacancy point defects into agglomerated defects occurs during the period of time between the formation of the region and the reduction of the concentration of vacancies in the region, and (iv) quench cooling the region through the temperature range at which agglomerated interstitials may nucleate to prevent the formation of agglomerated interstitials.

Other objects and features of this invention will be in part apparent and in part pointed out hereinafter.

DETAILED DESCRIPTION OF THE PREFERRED EMBODIMENTS

Figure 1:
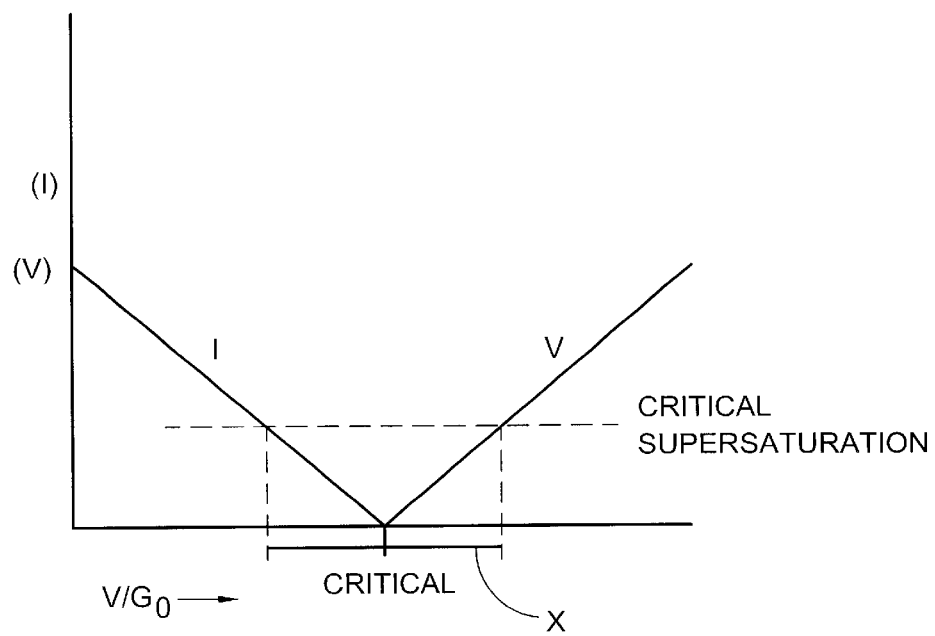
FIG. 1 is a graph which shows an example of how the initial concentration of self-interstitials, [I], and vacancies, [V], changes with an increase in the value of the ratio $v/G_0$, where v is the growth velocity and $G_0$ is the average axial temperature gradient.
Figure 2:
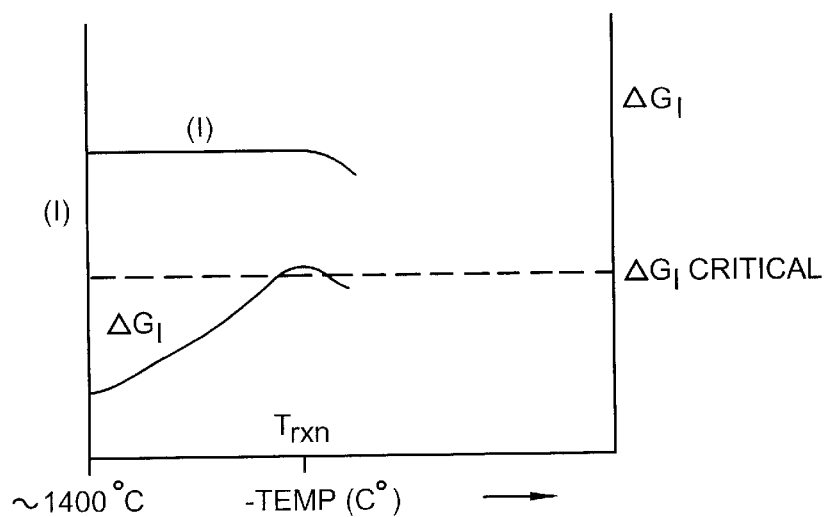
FIG. 2 is a graph which shows an example of how $\Delta G_I$, the change in free energy required for the formation of agglomerated interstitial defects, increases as the temperature, T, decreases, for a given initial concentration of self-interstitials, [I].
Figure 3:
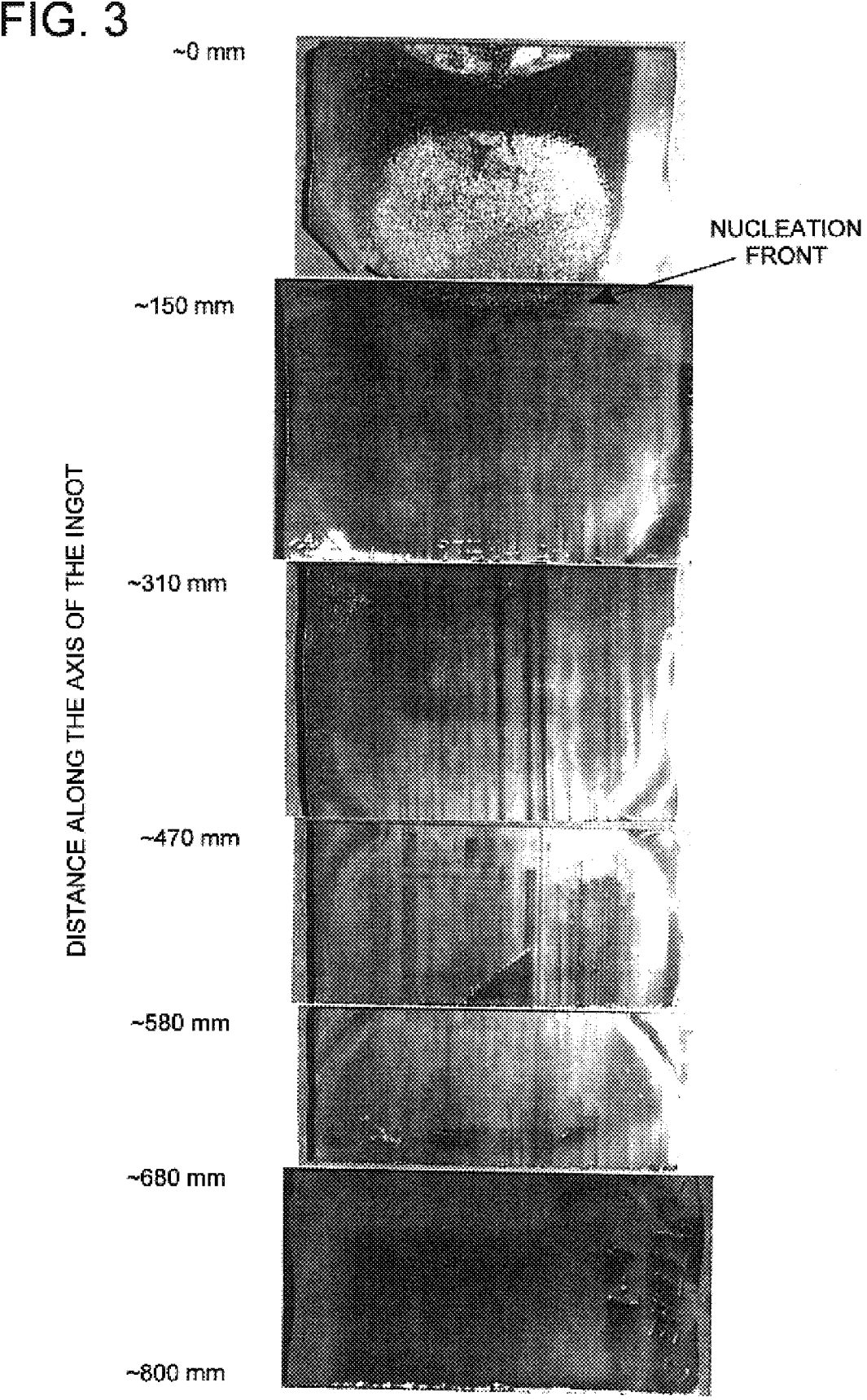
FIG. 3 is a cross-sectional image of an ingot prepared by quench cooling the ingot through the temperature range at which agglomerated intrinsic point defects nucleate.
Figure 4:
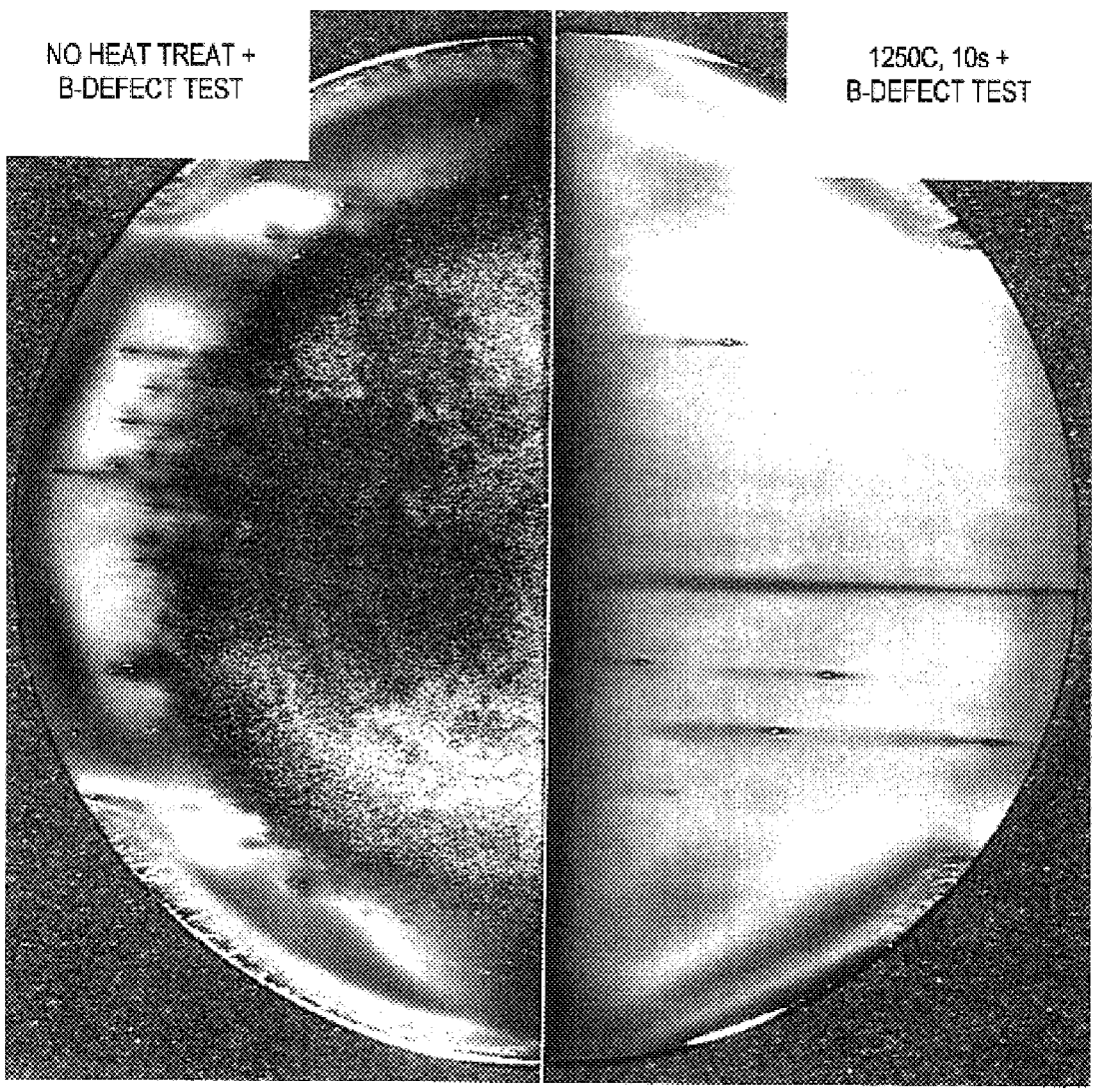
FIG. 4 is an image comparing a wafer having B-defects before being subjected to a B-defect annihilation heat-treatment to a wafer having B-defects which was subjected to a B-defect annihilation heat-treatment.

Based upon experimental evidence to-date, the type and initial concentration of intrinsic point defects appears to be initially determined as the ingot cools from the temperature of solidification (i.e., about 1410° C.) to a temperature greater than 1300° C. (i.e., at least about 1325° C., at least about 1350° C. or even at least about 1375° C.). That is, the type and initial concentration of these defects is believed to be controlled by the ratio $v/G_0$, where v is the growth velocity and $G_0$ is the average axial temperature gradient.

The transition between vacancy and interstitial dominated material occurs at a critical value of $v/G_0$ which, based upon currently available information, appears to be about $2.1 \times 10^{-5}$ cm$^2$/sK where $G_0$ is determined under conditions in which the axial temperature gradient is constant within the temperature range defined above. At this critical value, the resulting concentrations of these intrinsic point defects are equal. If the value of $v/G_0$ exceeds the critical value, vacancies are the predominant intrinsic point defect and the concentration of vacancies increases with increasing $v/G_0$. If the value of $v/G_0$ is less than the critical value, silicon self-interstitials are the predominant intrinsic point defect and the concentration of silicon self-interstitials increases with decreasing $v/G_0$. For a given $G_0$, therefore, a decrease in the pull rate tends to increase the concentration of silicon self-interstitials and an increase in the pull rate tends to increase the concentration of vacancies.

Once the initial concentration of an intrinsic point defect is established, the formation of agglomerated defects is thought to be dependent upon the free energy of the system. For a given concentration of intrinsic point defects a decrease in temperature yields an increase in the change in free energy for the reaction which forms agglomerated defects from the intrinsic point defects. Thus, as a region containing a concentration of vacancies or interstitials cools from the temperature of solidification through the temperature at which agglomerated defects are nucleated, the energy barrier for the formation of agglomerated vacancy or interstitial defects is approached. As cooling continues, this energy barrier may eventually be exceeded, at which point an agglomeration reaction occurs (See, e.g., Falster et al., U.S. Pat. No. 5,919,302 and Falster et al., WO 98/45509).

Surprisingly, it has been found that single crystal silicon ingots can be pulled at high growth rates which initially produce relatively high concentrations of vacancies and these concentrations may be suppressed by injecting interstitials from the lateral surface of the ingot before an agglomeration reaction occurs. In general, silicon self interstitial atoms may be injected by heating the lateral surface of the ingot to a temperature in excess of the temperature of the interior of the ingot, thereby causing a thermal gradient from the surface towards the interior. In one embodiment, the concentration of vacancies is merely reduced by this injection. In another embodiment, the number of injected silicon self-interstitial atoms is sufficient to convert the silicon from vacancy dominated to silicon self-interstitial dominated silicon.

In the process of the present invention, therefore, an ingot having a constant diameter region with a nominal diameter of at least about 125 mm, more preferably at least about 150 mm, and typically at least about 200 mm or even at least about 300 mm is grown at a pull rate to initially produce at least one region which is vacancy dominated (i.e., grown under conditions wherein the value of $v/G_0$ at some point along the radius and axis of the ingot is greater than the critical value of $v/G_0$). The vacancy dominated region may vary dimensionally both in the radial and axial direction.

Under typical Czochralski crystal growth conditions, the crystal growth velocity, v, is approximately constant as a function of radial distance from the crystal axis, but $G_0$ generally decreases from a maximum value at the crystal axis to a minimum value at the lateral surface of the ingot. As a result, the concentration of crystal lattice vacancies generally decreases with increasing radial distance from the ingot axis and a region of vacancy dominated silicon, if present at all, will occupy an axially symmetric region between the axis of the ingot and some radial distance, $R_v$, measured from the axis of the ingot. Preferably, $R_v$ has a value of at least about 1%, more preferably at least about 5%, more preferably at least about 10%, more preferably at least about 25%, more preferably at least about 50%, more preferably at least about 75%, and still more preferably at least about 90% of the radius of the constant diameter portion of the ingot.

Because $v/G_0$ may change as a function of axial position as a result of variations in v, $G_0$ or both v and $G_0$, the width of the axially symmetric region of vacancy dominated silicon may change as a function of axial position. Stated another way, the radial width of the vacancy-dominated axially symmetric region may increase or decrease as a function of axial position. For example, in one embodiment variations in $v/G_0$ during the growth of the constant diameter portion of the ingot may initially produce a single vacancy dominated region having an axial length which is equal to or less than the axial length of the constant diameter portion of the ingot; that is, the vacancy dominated axially symmetric region has an axial length of at least about 1%, more preferably at least about 5%, more preferably at least about 10%, more preferably at least about 25%, more preferably at least about 50%, more preferably at least about 75%, and still more preferably at least about 90% of the axial length of the constant diameter portion of the ingot. In general, this embodiment is preferred since it allows for the maximum growth rate, v, during the growth of the constant diameter portion of the crystal. Although presently less preferred, in other embodiments, it may be desirable to initially have a plurality (e.g., at least 2, 3, 4, 5, 6, 7, 8, 9 or even 10) discontinuous vacancy dominated regions separated by interstitial dominated region(s). Regardless of whether there is initially one or a plurality of vacancy dominated regions within the constant diameter portion of the ingot, it is generally preferred that the aggregate volume of the initial vacancy dominated axially symmetric region(s) in the constant diameter portion of the ingot occupy at least about 1%, more preferably at least about 5%, more preferably at least about 10%, more preferably at least about 25%, more preferably at least about 50%, more preferably at least about 75%, and still more preferably at least about 90% of the volume of the constant diameter portion of the ingot.

As the ingot is being grown, the previously solidified section of the ingot is generally allowed to cool. In the process of the present invention, however, the vacancy dominated region is maintained at a temperature in excess of the temperature at which agglomerated vacancy defects form until the lateral surface of the ingot is heated to inject silicon self-interstitials into this region. In general, the nucleation temperature increases with increasing concentration of intrinsic point defect. In addition, the range of nucleation temperatures for agglomerated vacancy-type defects is somewhat greater than the range of nucleation temperatures for agglomerated interstitial-type defects; stated another way, over the range of vacancy concentrations typically produced in Czochralski grown single crystal silicon the nucleation temperature for agglomerated vacancy defects is generally between about 1,000° C. and about 1,200° C. and typically between about 1,000° C. and about 1,100° C. whereas over the range of silicon self-interstitial concentrations typically produced in Czochralski grown single crystal silicon, the nucleation temperature for agglomerated interstitial defects is generally between about 850° C. and about 1,100° C. and typically between about 870° C. and about 970° C.

After allowing the vacancy dominated region to cool to a temperature greater than the temperature at which vacancies may nucleate, the lateral surface of the ingot or a portion thereof is reheated; that is, after initially being allowed to cool, heat is applied to the lateral surface in order to create a thermal gradient between the lateral surface and the interior of the ingot. Typically, the surface is heated to a temperature sufficient to create a thermal gradient of at least about 10° C./cm (as measured from the surface of the ingot towards the vacancy dominated region), with gradients of at least about 20° C./cm, 30° C./cm, 40° C./cm, 50° C./cm or more being preferred. Accordingly, the lateral surface is heated to a temperature of at least about 1200° C., more preferably at least about 1250° C., and most preferably at least about 1300° C. but less than about the solidification temperature of silicon (i.e., about 1410° C.). As a practical matter, however, it is difficult to heat the lateral surface to near the solidification temperature of silicon and still induce the desired thermal gradient. Therefore, although the lateral surface may be heated to a temperature range of about 1200° C. to about 1400° C., the lateral surface is more preferably heated to a temperature ranging from about 1300° C. to about 1375° C., and most preferably from about 1325° C. to about 1350° C.

Because, the temperature of the ingot prior to heating the lateral surface typically increases along the radius of the ingot from the lateral surface towards the axis of the ingot such that the lateral surface is at a temperature lower than the interior of the ingot, it is possible that, upon heating the lateral surface, a thermal gradient may be created between the lateral surface and a region at a distance less than the radius of the ingot, and in fact may exist only over a distance extending between the lateral surface and a region at a distance less than the distance from the lateral surface to the outer boundary of the vacancy dominated region. As a result, the thermally induced inward flux of interstitials may extend over only about 20%, 40%, 60%, 80% or more of the radius. Although the temperature gradient may not extend from the lateral surface to the vacancy dominated region, it is believed that the concentration gradient of silicon self interstitials will provide sufficient driving force to cause the thermally induced flux of interstitials to extend beyond the temperature gradient such that the interstitials continue to diffuse beyond the temperature gradient towards the vacancy dominated region. Stated differently, once the interstitials are created by the thermal gradient, they will continue to diffuse to areas of lesser concentration and therefore diffuse to the vacancy dominated region.

Heating the lateral surface of the ingot according to the conditions described above results in an increase in the concentration of interstitials at the lateral surface, $C_{is}$. The interstitials will then diffuse towards the interior of the ingot. As the interstitials diffuse into the vacancy dominated region, some of the interstitials will combine with vacancies, causing the concentration of vacancies, $C_v$, to be reduced, and the concentration of interstitials, $C_i$, to increase. Continued heating of the later surface and maintaining a temperature gradient therein will continue the flux of interstitials such that the interstitial concentration in the interior, $C_i$, would eventually reach, by in-diffusion, the same value $C_{is}$ as the equilibrium concentration at the surface. Thus, the interstitial solution in the interior of the ingot will become super-saturated by a factor of $S=C_{is}/C_{ie}$ since equilibrium concentration of the interior, $C_{ie}$, is below the surface value $C_{is}$.

In the process of achieving this, the vacancies in the vacancy dominated region will be annihilated, thus reducing the concentration of vacancies, $C_v$, in the vacancy dominated region. Accordingly, a vacancy under-saturation, by the same factor S, will be established. Given a sufficient influx of interstitials to the vacancy dominated region, the vacancy dominated region may be transformed to an interstitial dominated region wherein $C_i > C_v$.

Without being held to a particular theory, it is believed that at some point in time during the interstitial injection process there exists a vacancy annihilation front at a distance, $r_o$, from the axis of the ingot such that there remains a vacancy dominated region, having a radius $r_o$, of not yet annihilated initial vacancies and an annular region concentrically positioned around the remaining vacancy dominated region having a minimum radius of $r > r_o$ wherein the vacancies initially present have already been annihilated. The interstitial concentration $C_i$ at the annihilation front (at $r = r_o$) is much less than at the crystal surface (where it is of equilibrium value, $C_{is}$). Accordingly there is a radial in-flux of interstitials; the concentration field can be treated as quasi-steady-state, and so described by a conventional expression for cylindrical geometry wherein:

$$C_i = C_{is} ln(r/r_o)/ln(R/r_o) \tag{1}$$

where R is the radius of the ingot.

The total in-flux of interstitials to the vacancy dominated region, Q, is defined as:

$$Q = 2\pi D_i C_{is}/ln(R/r_o) \tag{2}$$

The vacancy dominated region decreases in diameter due to the in-flux Q of interstitials according to equation (3) such that:

$$d(\pi r_o^2 C_v)/dt = -Q \tag{3}$$

Furthermore, by substituting Equation (2) into equation (3) and balancing the resulting equation, the kinetic reduction in the radius of the vacancy dominated region may be described as follows:

$$r_o ln(R/r_o) dr_o/dt = -D_i C_{is}/C_v \tag{4}$$

Which can be further simplified to:

$$(r_o/R)^2 ln[(r_o/R)^2/e] = -1 + (4D_i C_{is}/R^2 C_v) \, t \tag{5}$$

Thus the time period required to completely annihilate the vacancy dominated region, referred to hereinafter as the annihilation time, $t_a$, occurs when the radius of the vacancy dominated region is reduced to zero such that $r_o = 0$ in equation (5) yielding the expression:

$$t_a = R^2 C_v/4D_i C_{is} \tag{6}$$

Thus, the annihilation time is dependent on the concentration of vacancies, $C_v$, the diameter of the ingot, R, and the self-diffusion product $D_i C_{ie}$ which is strongly dependant on the temperature. The temperature should therefore be as high as possible to increase the self-diffusion product and reduce the annihilation time. For example, the vacancy annihilation time for a 150 mm ingot having a typical vacancy concentration has been determined to be at least about 160 hours when the lateral surface is heated to a temperature of about 1200° C., at least about 45 hours when the lateral surface is heated to a temperature of about 1250° C., and at least about 14 hours when the lateral surface is heated to a temperature of about 1300° C., to completely annihilate the vacancy dominated region. Furthermore, larger diameter ingots require heating the lateral surface for longer periods of time at a given temperature compared to smaller diameter ingots. For example, the vacancy annihilation time for a 200 mm ingot is at least about 284 hours when the lateral surface is heated to a temperature of about 1200° C., at least about 80 hours when the lateral surface is heated to a temperature of about 1250° C., and at least about 25 hours when the lateral surface is heated to a temperature of about 1300° C. The vacancy annihilation time for a 300 mm ingot is at least about 640 hours when the lateral surface is heated to a temperature of about 1200° C., at least about 180 hours when the lateral surface is heated to a temperature of about 1250° C., and at least about 56 hours when the lateral surface is heated to a temperature of about 1300° C. Accordingly, the lateral surface is preferably heated for a time period of at least about 10 hrs, at least about 25 hrs, at least about 30 hrs, at least about 100 hrs and may even be heated for a time period of at least about 500 hours or greater.

The annihilation time may be significantly reduced by converting the ingot to a "semi-perfect" type. That is, an ingot wherein only a portion of the vacancy dominated region is transformed into an interstitials dominated region. The expression for the required anneal time to convert a semi-perfect crystal may be obtained by replacing R, the crystal radius, with $(R-R_{v/I})$, where $R_{v/I}$ is the radius of the v/I boundary position. The required time is reduced by a factor of the square of the ratio of these two numbers. In this regard, it is to be noted that the duration of heating, and therefore interstitial injection, may be other than described above. Preferably, however, the entire vacancy dominated regions is annihilated such that the resulting region is converted to an interstitial dominate region.

It is to be further noted that in the event the region becomes interstitial dominated, continued application of heat may result in the concentration of interstitials increasing to a level greater than the concentration required for the nucleation of agglomerated interstitial defects upon cooling of the ingot. As noted earlier, however, the nucleation of agglomerated interstitial defects may be prevented or alternatively, suppressed such that only the B-type defects are formed. Thus, heating the lateral surface for time periods in excess of those stated herein merely results in an increase in the concentration of interstitials which can subsequently be suppressed as described below.

According to the process of the present invention, the lateral surface may be heated using any means known in the art for heating silicon to temperatures in excess of 1200° C., provided a temperature gradient of at least 10° C./cm can be maintained for a sufficient period of time as described above. As a practical matter therefore, it is not desirable to heat the entire external surface of the ingot simultaneously. It is believed that in order to achieve and maintain the required temperature gradient, the heat in the center of the ingot must be allowed to escape axially. Heating the entire ingot simultaneously would prevent such a cooling path for the center of the ingot, and the ingot would eventually heat to a constant temperature, thus eliminating the temperature gradient. Preferably therefore, a ring heater is used to heat the lateral surface, wherein the ring heater and the lateral surface are caused to move relative to each other such that the entire lateral surface is eventually heated according to the conditions stated above. The ring heater may be concentrically positioned around the ingot in a fixed position within the growth chamber such that as the ingot is pulled from the melt, the lateral surface is caused to pass through the ring heater. Alternatively, the ring heater may be concentrically positioned around the ingot within the growth chamber such that it may be raised or lowered in the direction of the axis of the ingot. Additionally, the ring heater may be positioned in the pulling chamber in a fixed position concentric to the axis of the ingot such that the lateral surface passes through the ring heater as it is pulled into the pulling chamber, or, it may be movable along the axis of the ingot such that the ingot may be raised into the pulling chamber, after which the ring heater may be passed along the axis of the ingot such that the lateral surface is heated as required by the present invention.

Given the length of the ring heater or more precisely, the length, L, of the portion of the lateral surface that is heated by the hot zone of the ring heater and the relative velocity of the ring heater to the ingot, V, the dwell time of a lateral surface may be calculated as L/V. Stated differently, there exists a relationship between the length of the portion of the lateral surface heated by the ring heater, the velocity of the ring heater relative to the ingot, and the dwell time at which the lateral surface is heated such that dwell time equals L/V. Thus once the temperature and duration of the heating is determined, persons skilled in the art may determine the relative velocity at which the ring heater and the lateral surface must move. Practically speaking, the length L can not be much larger than one ingot diameter since the radial in-flux of heat, from the hot surface to the colder interior must be removed from the center of the ingot in the axial direction to maintain the required temperature gradient as described above.

For example, in the case of a 150 mm ingot wherein the lateral surface is to be heated to a temperature of 1300° C. for a period of 14 hours as described above, using a maximum length ring heater wherein L is about 150 mm, the velocity of the ring heater relative to the lateral surface must be about 0.17 mm/min or less. For an ingot wherein the constant diameter portion of the ingot is 1000 mm in length, the total anneal time is about 100 hr to heat a lateral surface extending along the entire length of the constant diameter portion of the ingot. Although this approach remains a practical alternative where the lateral surface is heated after the ingot is fully grown, the required velocity is much less than the desired pull rate to produce the vacancy dominated region and thus maximize the throughput of a crystal puller. Accordingly, a single ring heater would have to move in the axial direction during the growth of the ingot such that the velocity of the heater relative to the lateral surface produces the required dwell time as discussed above. However, under such conditions, the ingot would have to remain in the crystal puller after the growth of the ingot was completed until the annealing process was finished. For example in the example above, the annealing process would take 100 hours whereas the constant diameter portion of the ingot would be completed in less than 17 hours at a typical pull rate of 1.0 mm/min. Therefore, the throughput of the crystal puller would be substantially reduced.

In another embodiment of the present invention, several ring heaters may be used to significantly reduce to total time required to anneal the lateral surface along the entire axis of the constant diameter portion of the ingot. Furthermore, the heaters could be controlled to move along the axis of the ingot during the growth of the ingot such that the required heating conditions are met. Thus, assuming the ring heaters were identical, the time calculated above would be reduced by a factor equal to the number of ring heaters. Practically speaking these heater elements would have to be spaced by some distance greater than a crystal diameter in order to provide for axial cooling at the center of the ingot to enable the required thermal gradient to be maintained. Thus a maximum number of ring heaters having a length equal to the crystal diameter is equal to the length of the constant diameter portion of the ingot divided by two times the length of the heater. For example, for a 150 mm ingot having a constant diameter portion that is 1000 mm in length, the maximum number of ring heaters having a length equal to about 150 mm would be approximately 6. Using 6 ring heaters would effectively reduce the total time required to heat the entire lateral surface to about 17 hours. The precise length of the various ring heaters and the spacing between ring heaters may be varied without departing from the scope of the present invention.

It is to be noted, that the lateral surface may be heated during the growth of the ingot, immediately after the growth of the ingot, or may not be heated for substantially long periods of time after the growth of the ingot, provided the vacancy dominated region is maintained above the temperature at which agglomerated intrinsic point defects nucleate. Accordingly, the vacancy dominated region may be maintained above the nucleation temperature until such time as the lateral surface is heated to cause the injection of silicon self interstitials towards the region. In this manner, the ingot may be removed from the crystal puller, to another location, such that the crystal puller may be cooled to allow for the growth of a subsequent ingot, thus decoupling the interstitial injection process from the crystal growth process. In this manner, either a single ring heater, or multiple ring heaters may be used to heat the lateral surface for the proscribed time period as discussed above without effecting the throughput of the crystal puller.

Once the concentration of vacancies in the region have been reduced, preferably below the concentration at which agglomerated vacancies may nucleate upon cooling, or alternatively once the vacancy dominated region is converted to an interstitial dominated region, wherein the concentration of silicon self-interstitials is preferably less than the concentration at which agglomerated interstitials may nucleate upon cooling, the region may be cooled such that the resulting ingot is substantially free of any agglomerated intrinsic point defects.

Depending upon the resulting concentration and distribution of vacancies and self-interstitial atoms in the ingot, the formation of agglomerated intrinsic point defects may thereafter be avoided by controlling the diffusion of the intrinsic point defects and/or by quench cooling the ingot. Thus, if the flux of silicon self-interstitials is maintained such that the resulting concentration of vacancies or silicon self-interstitials is below the concentration at which vacancies or silicon self-interstitials may agglomerate upon cooling, the region may be allowed to cool by the standard Czochralski process. If, however the region or a portion thereof is converted to an interstitial dominated region, and the concentration of interstitials is greater than the concentration at which the interstitials may agglomerate upon cooling, or if a portion or all of the region has a concentration of vacancies greater than the concentration at which the vacancies may agglomerate upon cooling, the cooling rate of the region may be controlled such that the interstitials are permitted to diffuse to the surface of the ingot and/or diffuse towards and recombine with vacancies in the vacancy dominated regions thereby suppressing the concentration of vacancies and or interstitials during cooling such that the resulting ingot is substantially free of agglomerated intrinsic point defects (See for example co-pending U.S. patent application Ser. Nos. 09/344,036 and 09/344,709, both incorporated herein by reference.) Additionally, if the concentration of vacancies or silicon self-interstitials is greater than the concentration at which the vacancies or silicon self-interstitials may agglomerate upon cooling, the region may be quench cooled such that the vacancies or silicon self-interstitials are effectively frozen in position without allowing sufficient time for them to agglomerate, such that the resulting ingot is substantially free of agglomerated intrinsic point defects as described in co-pending U.S. Provisional Application No. 60/155,725 incorporated herein by reference.

Alternatively, the concentration of interstitials in the region after the injection of interstitials may be such that upon cooling, the region contains some agglomerated interstitial type defects, wherein the agglomerated interstitial-type defects are either B-type defects only, or are B-type and A-type defects. It should be noted that the region may even be cooled such that the resulting ingot has a reduced quantity of agglomerated vacancy-type intrinsic point defects compared to the quantity that would have occurred provided the ingot was produced without thermally inducing the flux of silicon self interstitials into the vacancy dominated region without departing from the scope of the present invention. However, as a practical matter, it is preferred that the resulting ingot be substantially free of agglomerated vacancy-type defects, and even more preferred that the ingot be substantially free of both agglomerated vacancy and interstitial type defects, i.e., substantially free of agglomerated intrinsic point defects.

In general, control of the average axial temperature gradient, $G_0$, may be achieved primarily through the design of the "hot zone" of the crystal puller, i.e. the graphite (or other materials) that makes up the heater, insulation, heat and radiation shields, among other things. Although the design particulars may vary depending upon the make and model of the crystal puller, in general, $G_0$ may be controlled using any of the means currently known in the art for controlling heat transfer at the melt/solid interface, including reflectors, radiation shields, purge tubes, light pipes, and heaters. In general, radial variations in $G_0$ are minimized by positioning such an apparatus within about one crystal diameter above the melt/solid interface. $G_0$ can be controlled further by adjusting the position of the apparatus relative to the melt and crystal. This is accomplished either by adjusting the position of the apparatus in the hot zone, or by adjusting the position of the melt surface in the hot zone. In addition, when a heater is employed, $G_0$ may be further controlled by adjusting the power supplied to the heater. Any, or all, of these methods can be used during a batch Czochralski process in which melt volume is depleted during the process.

The pull rate is dependent upon both the crystal diameter and crystal puller design. Pull rates for conventional crystal pulling processes are typically 0.5 mm/minute to 1.0 mm/minute for 200 mm diameter crystals and 0.3 mm/minute to 0.7 mm/minute for 300 mm diameter crystals. The present invention however allows for pull rates as high about 0.8 mm/minute, about 1 mm/minute, about 1.5 mm/minute, about 2 mm/minute and even as high as about 3 mm/minute or greater. It is to be noted that pull rates greater than 3 mm/minute typically push the practical limits of current crystal puller designs. However, the crystal puller may be designed to allow pull rates in excess of those stated here. As a result, most preferably the crystal puller will be designed to enable the pull rate to be as fast as possible provided they result in the formation of a single crystal silicon ingot.

Because the present invention preferably utilizes high growth rates, allowing for vacancy dominated regions and provides a means for suppressing the vacancy concentration after solidification and prior to cooling the ingot, the growth process not only allows for greater throughput, but is also more robust, allowing more process variability than prior art processes. For example, during the growth of an ingot $G_0$ may change as parts become coated and inaccurate pull rate calibration and diameter fluctuations can lead to variations in the pull, all of which can lead to variations in $v/G_0$ as a function of ingot. Similarly, aging of puller parts can result in crystal to crystal variation for crystals grown in the same crystal puller even though identical growth conditions were intended. Thus, processes carried out in accordance with the present invention are capable of consistently producing silicon ingots which are substantially free of agglomerated defects even though $v/G_0$ may vary as a function of crystal length or from crystal to crystal over any $v/G_0$ value capable of producing a single crystal silicon ingot have vacancies as the initial predominant intrinsic point defect.

Definitions

It is to be noted that, as used herein, the following phrases shall have the given meanings: "agglomerated intrinsic point defects" shall mean defects caused (i) by the reaction in which vacancies agglomerate or (ii) by the reaction in which self-interstitials agglomerate; "agglomerated vacancy defects" shall mean agglomerated vacancy point defects caused by the reaction in which crystal lattice vacancies agglomerate, examples include D-defects, flow pattern defects, gate oxide integrity defects, crystal originated particle defects, and crystal originated light point defects; "agglomerated interstitial defects" shall mean agglomerated intrinsic point defects caused by the reaction in which silicon self-interstitial atoms agglomerate to form A-defects (including dislocation loops and networks) and B-defects; "B-defects" shall mean agglomerated interstitial defects which are smaller than A-defect and which are capable of being dissolved if subjected to a heat treatment as further described herein; "radius" shall mean the distance measured from a central axis to a circumferential edge of a single crystal silicon sample, such as a wafer, or an ingot slug or slab; "substantially free of agglomerated intrinsic point defects" shall mean a concentration of agglomerated defects which is less than the detection limit of these defects, which is currently about $10^4$ defects/cm$^3$; "vacancy dominated" and "self-interstitial dominated" shall mean material in which the intrinsic point defects are predominantly vacancies or self-interstitials, respectively; and, "visual detection of agglomerated intrinsic point defects," as well as variations thereof, shall refer to the detection of such defects using the naked eye under ordinary incandescent or fluorescent light sources, or optionally collimated or other enhanced light sources, and without the use of any instrumentation which would otherwise aid in defect detection or result in defect magnification, such as optical or infrared microscopy, X-ray diffraction, or laser scattering.

Detection of Agglomerated Defects

Agglomerated defects may be detected by a number of different techniques. For example, flow pattern defects, or D-defects, are typically detected by preferentially etching the single crystal silicon sample in a Secco etch solution for about 30 minutes, and then subjecting the sample to microscopic inspection. (see, e.g., H. Yamagishi et al., Semicond. Sci. Technol. 7, A135 (1992)). Although standard for the detection of agglomerated vacancy defects, this process may also be used to detect A-defects. When this technique is used, such defects appear as large pits on the surface of the sample when present.

Additionally, agglomerated intrinsic point defects may be visually detected by decorating these defects with a metal capable of diffusing into the single crystal silicon matrix upon the application of heat. Specifically, single crystal silicon samples, such as wafers, slugs or slabs, may be visually inspected for the presence of such defects by first coating a surface of the sample with a composition containing a metal capable of decorating these defects, such as a concentrated solution of copper nitrate. The coated sample is then heated to a temperature between about 900° C. and about 1000° C. for about 5 minutes to about 15 minutes in order to diffuse the metal into the sample. The heat treated sample is then cooled to room temperature, thus causing the metal to become critically supersaturated and precipitate at sites within the sample matrix at which defects are present.

After cooling, the sample is first subjected to a non-defect delineating etch, in order to remove surface residue and precipitants, by treating the sample with a bright etch solution for about 8 to about 12 minutes. A typical bright etch solution comprises about 55 percent nitric acid (70% solution by weight), about 20 percent hydrofluoric acid (49% solution by weight), and about 25 percent hydrochloric acid (concentrated solution).

The sample is then rinsed with deionized water and subjected to a second etching step by immersing the sample in, or treating it with, a Secco or Wright etch solution for about 35 to about 55 minutes. Typically, the sample will be etched using a Secco etch solution comprising about a 1:2 ratio of 0.15 M potassium dichromate and hydrofluoric acid (49% solution by weight). This etching step acts to reveal, or delineate, agglomerated defects which may be present.

In an alternative embodiment of this "defect decoration" process, the single crystal silicon sample is subjected to a thermal anneal prior to the application of the metal-containing composition. Typically, the sample is heated to a temperature ranging from about 850° C. to about 950° C. for about 3 hours to about 5 hours. This embodiment is particularly preferred for purposes of detecting B-type silicon self-interstitial agglomerated defects. Without being held to a particular theory, it is generally believed that this thermal treatment acts to stabilize and grow B-defects, such that they may be more easily decorated and detected.

Agglomerated vacancy defects may also be detected using laser scattering techniques, such as laser scattering tomography, which typically have a lower defect density detection limit that other etching techniques.

In general, regions of interstitial and vacancy dominated material free of agglomerated defects can be distinguished from each other and from material containing agglomerated defects by the copper decoration technique described above. Regions of defect-free interstitial dominated material contain no decorated features revealed by the etching whereas regions of defect-free vacancy dominated material (prior to a high-temperature oxygen nuclei dissolution treatment as described above) contain small etch pits due to copper decoration of the oxygen nuclei.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

What is claimed is:

1. A process for the preparation of a silicon single crystal in which molten silicon is solidified onto a crystal in accordance with the Czochralski method to form an ingot having a central axis, a seed-cone, an end-cone, a constant diameter portion between the seed-cone and the end-cone having a lateral surface, and a radius extending from the central axis to the lateral surface, the process comprising:

forming a region within the constant diameter portion in which vacancies are the predominant intrinsic point defect;

heating the lateral surface of the ingot to a temperature in excess of the temperature of the region to cause an inward flux of silicon self interstitial atoms into the region from the heated surface which reduces the concentration of vacancies in the region; and.

maintaining the temperature of the region in excess of the temperature, $T_A$, at which agglomeration of vacancy point defects into agglomerated defects occurs during the period of time between the formation of the region and the influx of the silicon self-interstitial atoms from the lateral surface, wherein the length of the lateral surface, as measured in the axial direction, which is coincidentally heated to a temperature in excess of the temperature of the region to cause an inward flux of silicon self interstitial atoms into the region from the heated surface is no greater than about 50% of the axial length of the constant diameter portion of the ingot.

2. The process of claim 1 wherein the region is symmetric about the axis of the constant diameter portion of the ingot and has an axial length of at least about 50% of the length of the constant diameter portion of the ingot.

3. The process of claim 2 wherein the region is symmetric about the axis of the constant diameter portion of the ingot and has a radial width of at least about 10% of the radius.

4. The process of claim 2 wherein the region is symmetric about the axis of the constant diameter portion of the ingot and has a radial width of at least about 50% of the radius.

5. The process of claim 1 wherein the length of the lateral surface, as measured in the axial direction, which is coincidentally heated to a temperature in excess of the temperature of the region to cause an inward flux of silicon self interstitial atoms into the region from the heated surface is no greater than about 25% of the axial length of the constant diameter portion of the ingot.

6. The process of claim 1 wherein the region is symmetric about the axis of the constant diameter portion of the ingot and has a radial width of at least about 10% of the radius.

7. The process of claim 1 wherein the region is symmetric about the axis of the constant diameter portion of the ingot and has a radial width of at least about 50% of the radius.

8. The process of claim 1 wherein the region is symmetric about the axis of the constant diameter portion of the ingot and has an axial length of at least about 10% of the length of the constant diameter portion of the ingot.

9. The process of claim 8 wherein the region is symmetric about the axis of the constant diameter portion of the ingot and has a radial width of at least about 10% of the radius.

10. The process of claim 8 wherein the region is symmetric about the axis of the constant diameter portion of the ingot and has a radial width of at least about 50% of the radius.

11. The process of claim 1 wherein at least about 20% of the constant diameter portion of the ingot is formed before the lateral surface is heated to cause an inward flux of silicon self-interstitial atoms.

12. The process of claim 11 wherein the region is symmetric about the axis of the constant diameter portion of the ingot and has an axial length of at least about 10% of the length of the constant diameter portion of the ingot.

13. The process of claim 12 wherein the region is symmetric about the axis of the constant diameter portion of the ingot and has a radial width of at least about 10% of the radius.

14. The process of claim 12 wherein the region is symmetric about the axis of the constant diameter portion of the ingot and has a radial width of at least about 50% of the radius.

15. The process of claim 1 wherein a heater is used to heat the lateral surface, the heater encircles the ingot, and the heater and ingot are moved relative to each other along the axis of the ingot as the ingot is being grown by the Czochralski method.

16. The process of claim 1 wherein a heater is used to heat the lateral surface, the heater encircles the ingot, and the heater and ingot are moved relative to each other along the axis of the ingot after the ingot has been grown by the Czochralski method and detached from the melt.

17. The process of claim 1 wherein the surface is heated to a temperature in excess of about 1200° C., but less than the melting point of silicon.

18. The process of claim 1 wherein the surface is heated to a temperature of at least about 1300° C. to about 1375° C.

19. The process of claim 1 wherein the temperature of the region is maintained at a temperature of at least about 1100° C. or more during the period of time between the formation of the region and the influx of silicon self-interstitial atoms.

20. The process of claim 1 wherein the temperature of the region is maintained at a temperature of at least about 1150° C. or more during the period of time between the formation of the region and the influx of silicon self-interstitial atoms.

21. The process of claim 1 wherein the concentration of vacancies in the region after the heating step is insufficient to form agglomerated vacancy defects in the region independent of the cooling rate of the region from its temperature during the heating step to a temperature of no more than 1000° C.

22. The process of claim 1 the process further comprising cooling the region below the temperature at which the agglomeration of intrinsic point defects occurs over a time period which is sufficient to prevent the formation of agglomerated intrinsic point defects within the region.

23. The process of claim 1 the process further comprising rapidly cooling the region through the temperature range at which the agglomeration of intrinsic point defects occurs, the region being cooled at a rate of at least about 10° C./min.

24. A The process for the preparation of a silicon single crystal in which molten silicon is solidified onto a crystal in accordance with the Czochralski method to form an ingot having a central axis, a seed-cone, an end-cone, a constant diameter portion between the seed-cone and the end-cone having a lateral surface, and a radius extending from the central axis to the lateral surface, the process comprising:

forming a region within the constant diameter portion in which vacancies are the predominant intrinsic point defect;

heating the lateral surface of the ingot to a temperature in excess of the temperature of the region to cause an inward flux of silicon self interstitial atoms into the region from the heated surface which reduces the concentration of vacancies in the region, wherein the influx of silicon self-interstitial atoms is sufficient to make silicon self-interstitial atoms the predominant intrinsic point defect in the region; and maintaining the temperature of the region in excess of the temperature, $T_A$, at which agglomeration of vacancy point defects into agglomerated defects occurs during the period of time between the formation of the region and the influx of the silicon self-interstitial atoms from the lateral surface.

25. The process of claim 24 the process further comprising rapidly cooling the region through the temperature range at which the agglomeration of intrinsic point defects occurs, the region being cooled at a rate of at least about 10° C./min.

26. The process of claim 24 wherein the temperature of the region is maintained at a temperature of at least about 1150° C. or more during the period of time between the formation of the region and the influx of silicon self-interstitial atoms.

27. The process of claim 24 wherein the temperature of the region is maintained at a temperature of at least about 1100° C. or more during the period of time between the formation of the region and the influx of silicon self-interstitial atoms.

28. The process of claim 24 wherein a heater is used to heat the lateral surface, the heater encircles the ingot, and the heater and ingot are moved relative to each other along the axis of the ingot as the ingot is being grown by the Czochralski method.

29. The process of claim 24 wherein the concentration of silicon self-interstitial atoms in the region after the heating step is insufficient to form agglomerated interstitial type defects in the region independent of the cooling rate of the region from its temperature during the heating step to a temperature of no more than about 850° C.

30. The process of claim 24 wherein the concentration of silicon self-interstitial atoms in the region after the heating step is insufficient to form agglomerated interstitial type defects other than B-type defects in the region independent of the cooling rate of the region from its temperature during the heating step to a temperature of no more than about 850° C.

31. The process of claim 24 the process further comprising cooling the region below the temperature at which the agglomeration of intrinsic point defects occurs over a time period which is sufficient to prevent the formation of agglomerated intrinsic point defects within the region.

32. The process of claim 24 the process further comprising rapidly cooling the region through the temperature range at which the agglomeration of intrinsic point defects occurs, the region being cooled at a rate of at least about 10° C./min.

33. The process of claim 24 wherein the region is symmetric about the axis of the constant diameter portion of the ingot and has a radial width of at least about 10% of the radius.

34. The process of claim 24 wherein the region is symmetric about the axis of the constant diameter portion of the ingot and has a radial width of at least about 50% of the radius.

35. The process of claim 24 wherein the region is symmetric about the axis of the constant diameter portion of the ingot and has an axial length of at least about 10% of the length of the constant diameter portion of the ingot.

36. The process of claim 35 wherein the region is symmetric about the axis of the constant diameter portion of the ingot and has a radial width of at least about 10% of the radius.

37. The process of claim 35 wherein the region is symmetric about the axis of the constant diameter portion of the ingot and has a radial width of at least about 50% of the radius.

38. The process of claim 24 wherein the region is symmetric about the axis of the constant diameter portion of the ingot and has an axial length of at least about 50% of the length of the constant diameter portion of the ingot.

39. The process of claim 38 wherein the region is symmetric about the axis of the constant diameter portion of the ingot and has a radial width of at least about 10% of the radius.

40. The process of claim 38 wherein the region is symmetric about the axis of the constant diameter portion of the ingot and has a radial width of at least about 50% of the radius.

41. The process of claim 24 wherein a heater is used to heat the lateral surface, the heater encircles the ingot, and the heater and ingot are moved relative to each other along the axis of the ingot after the ingot has been grown by the Czochralski method and detached from the melt.

42. The process of claim 24 wherein the surface is heated to a temperature in excess of about 1200° C., but less than the melting point of silicon.

43. The process of claim 24 wherein the surface is heated to a temperature of at least about 1300° C. to about 1375° C.

44. The process of claim 24 wherein at least about 20% of the constant diameter portion of the ingot is formed before the lateral surface is heated to cause an inward flux of silicon self-interstitial atoms.

45. The process of claim 44 wherein the region is symmetric about the axis of the constant diameter portion of the ingot and has an axial length of at least about 10% of the length of the constant diameter portion of the ingot.

46. The process of claim 45 wherein the region is symmetric about the axis of the constant diameter portion of the ingot and has a radial width of at least about 10% of the radius.

47. The process of claim 45 wherein the region is symmetric about the axis of the constant diameter portion of the ingot and has a radial width of at least about 50% of the radius.

* * * * *

UNITED STATES PATENT AND TRADEMARK OFFICE
CERTIFICATE OF CORRECTION

PATENT NO. : 6,689,209 B2
DATED : February 10, 2004
INVENTOR(S) : Robert J. Falster It is certified that error appears in the above-identified patent and that said Letters Patent is hereby corrected as shown below:

Column 16,
Line 58, "A The process" should read -- A process --.

Column 17,
Line 8, "region; and" should read -- region; and, --.

Signed and Sealed this

Twenty-ninth Day of June, 2004

JON W. DUDAS
*Acting Director of the United States Patent and Trademark Office*